United States Patent
Palpu et al.

(10) Patent No.: US 7,687,081 B2
(45) Date of Patent: Mar. 30, 2010

(54) HERBAL FORMULATION USEFUL AS LOCAL ANESTHETIC

(75) Inventors: Pushpangadan Palpu, Lucknow (IN); Chandana Venkateswara Rao, Lucknow (IN); Ajay Kumar Singh Rawat, Lucknow (IN); Sanjeev Kumar Ojha, Lucknow (IN); Sharad Kumar Srivastava, Lucknow (IN); Subha Rastogi, Lucknow (IN); Vivek Kumar, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 1197 days.

(21) Appl. No.: 11/024,008

(22) Filed: Dec. 28, 2004

(65) Prior Publication Data

US 2006/0141064 A1   Jun. 29, 2006

(51) Int. Cl.
  *A61K 36/00* (2006.01)
  *A61K 36/10* (2006.01)
  *A61K 36/11* (2006.01)
(52) U.S. Cl. .................. 424/725; 424/762; 424/764

(58) Field of Classification Search ................. 424/725, 424/769
See application file for complete search history.

(56) References Cited

U.S. PATENT DOCUMENTS

| 4,427,116 | A | * | 1/1984 | Brown ........................ 206/530 |
| 5,316,760 | A | * | 5/1994 | Voerman ..................... 424/58 |
| 5,525,330 | A | * | 6/1996 | Gaffar et al. ................. 424/52 |
| 6,264,926 | B1 | * | 7/2001 | Farooqi et al. ............... 424/58 |

OTHER PUBLICATIONS

Hrnriette's Herbal Homepage, website www.henriettesherbal.com/plants/spilanthes-oleracea.*
Derwent 1988-180552, May 1988, Derwent, Hichi.*

* cited by examiner

*Primary Examiner*—Christopher R Tate
*Assistant Examiner*—Randall Winston
(74) *Attorney, Agent, or Firm*—Ladas and Parry LLP

(57) ABSTRACT

The invention provides a novel herbal formulation useful as local anesthetic in topical surgical operations, nerve block conduction, extradural and infiltration anesthesia. Formulation(s) comprises of extract(s) of *Spilanthus calva* and *Spilanthus oleraceae* with *Gymnema sylvestre*, *Urtica dioica* and *Piper longum*. The formulation can be used as topical application as ointment or spray or cream.

15 Claims, No Drawings

HERBAL FORMULATION USEFUL AS LOCAL ANESTHETIC

FIELD OF THE INVENTION

The present invention relates to a novel herbal formulation useful as local anaesthetic.

BACKGROUND AND PRIOR ART OF THE INVENTION

Local anaesthesia may be employed in hernia operations, either on its own or combined with general anaesthesia. The choice of technique will be influenced not only by local resources and skills, but also by patient preference. With a careful technique, local anaesthesia causes minimal physiological disturbance. This may be particularly useful for patients with cardiovascular or respiratory disease for whom there may be advantages in avoiding a general aesthetic. The absence of postoperative sedation or drowsiness allows early ambulation and diminishes the requirement for recovery facilities. Local anaesthesia provides postoperative analgesia for up to four hours and may be administered by the surgeon. When adrenaline is mixed with the local anaesthetic (normally in a dilution of 1:200,000) useful vasoconstriction is produced resulting in a relatively bloodless field.

The nerve supply to inguinal and femoral hernia comes from the anterior branches of the six lower intercostals nerves which continue forward on to the anterior abdominal wall accompanied by the last thoracic (subcostal) nerve. The iliohypogastric and ilioinguinal nerves (T12 and L1) supply the lower abdomen. They are blocked by an injection of local anaesthetic between internal and external oblique muscles just medial to the anterior superior iliac spine. The genitofemoral nerve (L1, 2) supplies inguinal cord structures and the anterior scrotum via its genital branch and supplies the skin and subcutaneous tissues of the femoral triangle via the femoral branch. Local anaesthetic agents are relatively free from side effects if they are administered in an appropriate dosage and in the correct anatomical location. However, systemic and localized toxic reactions may occur, usually from the accidental intravascular or intra-thecal injection, or the administration of an excessive dose of the local anaesthetic agent. Systemic reactions to local anaesthetics involve primarily the central nervous system and the cardiovascular system. The airway is maintained and oxygen administered by face-mask, using artificial ventilation if apnoea occurs. Convulsions are treated with anticonvulsant drugs such as thiopentone or diazepam repeated as necessary. Profound hypotension and brady-arrhythmias should be treated with intravenous atropine and colloid or crystalloid infusions as plasma expanders may be necessary. Occasionally adrenaline may be required for severe hypotension or bradycardia. The invention provides a novel herbal local anaesthetic used in minor surgery like tooth removal or in topical surgery or in hernia operations without any toxic symptoms.

OBJECT OF THE INVENTION

The main object of the present invention is to provide a novel herbal formulation useful as a local anaesthetic, for spinal anaesthesia and for membrane stabilizing properties.

Another objective of the present invention is to prepare herbal ointment/cream/gel form that improves and acts as local anaesthetic.

Yet another object of the present invention is to prepare herbal dosage from in the form of topical solution/spray for easy acceptablity.

SUMMARY OF THE INVENTION

Accordingly, the invention provides a novel herbal formulation useful as local anaesthetic. The herbal formulation is also useful for membrane stabilizing properties and in topical anaesthesia, nerve block conduction, extradural and infiltration anaesthesia.

In an embodiment an herbal local anesthetic synergistic formulation (s) containing extracts of plants in pharmacologically effective form.

In still another embodiment, herbal formulation(s) as claimed in claim 1 wherein the extracts/juice of the plants are mixed in the ratio viz. *Spilanthus calva* (1-3% wt), *Spilanthus oleraceae* (1-3% wt), *Urtica dioica* (2-3% wt), *Piper longum* (1-2% wt), *Gymnema sylvestre* (2-3% wt) and the balance being the conventional additives.

In yet another embodiment, the plant used is *Spilanthus calva*.

In still another embodiment, the plant used is *Spilanthus oleraceae*.

In an embodiment, the plant used is *Gymnema sylvestre*.

In still another embodiment, plant used is *Urtica dioica*.

In still another embodiment, the plant used is *Piper longum*.

In yet another embodiment, the extract of *Spilanthus calva* is obtained from leaves/roots/flowers/rhizome/fruits.

In yet another embodiment, the extract of *Piper longum* is obtained from fruit extract.

In still another embodiment, the extract of *Spilanthus oleraceae* is obtained from leaves/flowers/rhizome/unriped fruits.

In an embodiment, the extract of *Gymnema sylvestre* was aerial parts.

In yet another embodiment, the extract of plant *Spilanthus calva*, *Spilanthus oleraceae* and *Piper longum* are mixed along with an additive to provide a topical application and intradermal injection form.

In still another embodiment, the extracts of plant *Spilanthus calva*, *Spilanthus oleraceae*, *Urtica dioica*, *Piper longum* and *Gymnema sylvestre* are mixed in equal proportion along with conventional additives to form an topical and intradermal injection form.

In still another embodiment, the composition is a topical or ointment or spray form.

In yet another embodiment, the said formulation is use as an analgesic when applied for muscular pains and inflammation.

In still another embodiment, the formulation is used against toothache and gum trouble.

In yet another embodiment, the said formulation has specific gravity ranging between 0.897-1.127.

In still another embodiment, the formulation has refractive index ranging between 1.1325-1.3642.

In still another embodiment, the additives used in the cream/ointment selected from a group consisting of poly ethylene glycol bases, hydro emulsifying bases and bentonite.

In still another embodiment, the additives used in the intradermal injection being sterile water for injection.

In yet another embodiment, the additives used are water-soluble bases.

In an embodiment, the water-soluble base used are selected from a group consisting of tragacanth, pectin, acacia and gelatin.

In another embodiment of the invention the formulation at dose of 400 mg/kg did not show any toxicity in rats as well as no change in organ body weight.

In another embodiment of the invention the synergistic formulation at a dose ranging from 100-200 mg/kg is highly effective as local anaesthetic for around 5-7 min.

The present invention also provides a method of inducing anaesthesia, comprising the step of administering an effective amount of a herbal formulation to a subject together with or in combination with therapeutically acceptable additives.

In another embodiment of the invention, a herbal formulation comprising *Spilanthus calva* (3%) and *Spilanthus oleraceae*, (3%) with conventional additives at a dose ranging from 100-200 mg/kg being moderately effective as local anaesthetic for around 20 min.

In yet another embodiment of the invention a herbal formulation containing *Spilanthus calva* (3%), *Spilanthus oleraceae* (3%), *Gymnema sylvestre* (3%) with conventional additives at a dose ranging from 100-200 mg/kg being moderately effective as local anaesthetic for around 15 min.

The present invention also provides for the use of herbal formulation as an anaesthetic at a dose ranging from 100-200 mg/kg body weight is effective as local anaesthetic around for 5-20 min.

DETAILED DESCRIPTION OF THE INVENTION

The present invention provides novel herbal formulation useful as a local anaesthetic, spinal anaesthesia and membrane stabilizing properties obtained from *Spilanthus* spp. The herbal formulation comprising of *Spilanthus calva*, *Spilanthus oleraceae*, *Urtica dioica*, *Piper longum* and *Gymnema sylvestre*. It was shown that it produces a significant improvement in membrane stabilising local anaesthesia. The plants used in the invention have the following properties reported.

*Spilanthes calva* DC. Family-Compositae

Botanical Synonyms

*Spilanthes acmella* var. *calva* {DC.} C. B. Clarke, *S. acmella* auct. Non {L.} Murr.

Description

An annual herb up to 60 cm tall. Stems erect or decumbent at base, more or less hairy. Leaves opposite, triangular ovate or lanceolate, margins dentate or almost entire, sparsely pubescent beneath. Flower heads ovoid, pale yellow or white, long-peduncled, solitary or in terminal panicles. Achenes obovate to trigonous with ciliate edges.

Distribution and Habitat

Occurs in moist habitats in the plains and lower hill regions throughout India and Srilanka, Java and the Lesser Sunda Islands.

Medicinal Properties and Uses

The plant, boiled in water, is used to treat dysentery. The decoction is also given as a diuretic and lithotriptic and used as a bath for relieving rheumatism and as a lotion for scabies and psoriasis. The juice from the plant is a vulnerary. The pounded herb is used as a poultice to dress wounds. The pungent flower heads are chewed to relieve toothache and affection of the gums and throat, and paralysis of the tongue; it is used to treat stammering in children in western India. A tincture made from the flower heads is used as a substitute for the tincture of pyrethrum (prepared from the roots of *Anacyclus pyrethrum*: Asteraceae) to treat inflammation of the jaw and dental caries. The roots are purgative. The crushed plant is used as a fish poison.

*Spilanthes oleracea* L. Family-Compositae

Description

A perennial herb, closely related to *spilanthes calva*, but more robust, succulent, and with large flower heads. Leaves triangular or triangular-ovate, obtuse, attenuate below. Florets reddish-brown; achene's scabrid.

Distribution and Habitat

Introduced from Brazil and cultivated in gardens as an ornamental and for its pungent leaves which are used in salads. Sometimes naturalized.

Medicinal Properties and Uses

The whole plant is very acrid, the flower heads particularly so, causing profuse salivation when chewed. They are used to treat headaches, paralysis of the tongue, affections of the throat and gums, and for toothache. A tincture of the fresh as well as the dried herb is also used to relieve toothache, scurvy and gum troubles, and is taken internally to treat gout and bladder pain.

*Piper longum* L. Family-Piperaceae

Description

A slender, aromatic climber with perennial woody roots; stems jointed, creeping, young shoots downy. Leaves simple, alternate, 5-12 cm long and 3-6 cm wide, glabrous, ovate base cord ate with broad rounded lobes, apex sub acute, and margins entire. Flowers minute on unisexual, axillary, cylindrical spikes; green at first, turning yellow, up to 5 cm long; male spikes longer than female. Fruits ovoid, yellowish orange turning dark red to blackish, sunk in fleshy spikes 2.5-3.8 cm long. Flowers during the rainy season and fruits during the autumn.

Distribution and Habitat

Considered native to tropical and subtropical India, Nepal, Bangladesh, Myanmar (burma), and the Malay Peninsula. In India it is found from central Himalayan to Assam, the lower hills of west Bengal, and in the evergreen forest of peninsular India from konkan(Maharashtra)to Travancore(kerala).it is occasionally cultivated in north-eastern and southern India for its fruits, used as a spice and in pickles and preserves.

Medicinal Properties and Uses

The dried roots, as well as the immature and mature fruits, are used extensively, alone and in combination with other plant drug to treat a broad range of ailments in traditional Indian medicine. The dried roots and thicker stems, known commercially as piplamul, are an important drug in the ayurvedic and unani systems. The roots and fruits are used to treat dysentery and leucoderma, as a cholagogue for treating bileduct and gallbladder obstruction, and as a counter-irritant and analgesic for relieving muscularpains and inflammations. A decoction of dried immature fruit and root, or the powdered fruits mixed with honey, is used to treat chronic bronchitis, cough and cold. An infusion of the powdered fruits is given to women after childbirth to check bleeding and fever. It is as important ingredient in medicated oil used externally for sciatica and paraplegia.

*Urtica dioica* (Linn) Family: Urticaceae

Description

A genus of annual or perennial herbs, commonly known as nettle, distributed in the temperate and sub-tropical zones. Four species occur in India, of which *U. pilulifera*, an exotic herb, has become naturalized at many places. Several species of this genus are armed with stinging hairs on the leaves and stems, which, on contact with the skin, cause irritation and symptoms of urticaria or nettle rash. Sharp and fragile ends of the hairs penetrate the skin and break off and the irritating principles inside the hairs come in contact with the tissues, resulting in an uncomfortable itchy sensation accompanied by rash. Some nettles, such as *U. dioica* and *U. pilulifera*, yield a fibre, which is said to rival the best hemp in strength. Some others have been credited with diuretic properties in folk medicine.

Distribution and Habitat

A robust, dioecious herb, upto 2 m high, with grooved stems abundantly armed with stinging hair, found in the Himalayas from Kashmir to kumaun at altitudes of 2,100-3,200 m. leaves ovate or lanceolate, usually cordate, serrate; flowers greenish, in axillary cymes.

Medicinal properties and uses

Hemostatic, used in uterine hemorrhage, bleeding from the nose and vomiting of blood. Also used in sciatica and rheumatism. In USSR, leaves are used as a medicine known as alcohol, used for chronic hepatitis, cholengitis, habitual constipation and powerfully diuretic. Roots and seeds prescribed in diarrhoea and intestinal worms. Infusion of leaves and roots used as a hair-stimulant and for cleaning dandruff. Tender leaves and shoots consumed as a vegetable. Properly dried and cut up, the plant is used as fodder; rich in protein and mineral contents; recommended as a good chicken feed. Stems yield a fibre, which is said to rival the best hemp in strength. By careful dressing the fibre becomes as fine as silk. Seeds nutritious and source of a edible fatty oil. In rabbits, the oral and parenteral administration of a preparation of *U. dioica* showed hypoglycaemic effect. The irritant property of the nettle has long been used externally to excite activity in paralysed limbs and internally the treatment of haematoptysis and other haemorrhages.

*Gymnema sylvestre* (Retz.) Family-Asclepiadaceae

Description

A large stout, woody climber with densely appressed hairy branchlets, frequently covering the tops of trees. Leaves opposite, elliptic or obovate-acute, thinyly coriaceous, sometimes pubescent above, usually 2-6 cm long and 1-3 cm wide, base usually rounded, truncate or shallowly cordate, apex shortly acuminate; petioles 0.4-1.2 cm, densely pubescent. Flowers borne in crowded umbellate cymes; corolla yellow, 4-5 mm across, tube campanulate. Fruits (follicles) slender, cylindrical, lanceolate, glabrous, 6.3-7.6 cm long and 0.8 cm wide; seeds narrowly ovoid-oblong, flat with a broad thin wing, pale brown.

Distribution and habitat

Found in dry forests in the hill regions of Bihar, Orissa and Madhya Pradesh southwards through southern India to an elevation of 650 m. In central India it is most commonly found in open forests on soils derived from sandstone.

Medicinal Properties and Uses

The plant is considered antiperiodic, diuretic and stomachic. In Ayurvedic practice, the root and leaf are used to treat headache, hydrocele, polyuria, leprosy, pruritis, poisoning, wounds and bronchial asthma. The leaves are believed to be hypoglycaemic and are an important ingredient of Ayurvedic formulations for diabetes; they are also used to treat cough and fever. Among the Gonds of Andhra Pradesh, the filtered extract of the ground leaf twigs is taken orally to relieve malarial fever. The root is considered to possess astringent, emetic, expectorant, cooling, stomachic and tonic properties.

Accordingly, the invention provides a novel herbal formulation useful as local anaesthetic. The herbal formulation is also useful for membrane stabilizing properties and in topical anaesthesia, nerve block conduction, extradural and infiltration anaesthesia.

The herbal formulation when used as an anesthetic contains extracts of plants in pharmacologically effective form. The extracts/juice of the plants are mixed in the ratio viz. *Spilanthus calva* (1-3% wt), *Spilanthus oleraceae* (1-3% wt), *Urtica dioica* (2-3% wt), *Piper longum* (1-2% wt), *Gymnema sylvestre* (2-3% wt) and the balance being the conventional additives. The plant used is *Spilanthus calva* and/or *Spilanthus oleraceae*, and/or *Gymnema sylvestre* and/or *Urtica dioica* and/or *Piper longum*.

The extract of *Spilanthus calva* is obtained from leaves/roots/flowers/rhizome/fruits.

The extract of *Piper longum* is obtained from fruit extract.

The extract of *Spilanthus oleraceae* is obtained from leaves/flowers/rhizome/unriped fruits.

The extract of *Gymnema sylvestre* was aerial parts.

The extract of plant *Spilanthus calva*, *Spilanthus oleraceae* and *Piper longum* are mixed along with an additive to provide a topical application and intradermal injection form. The extracts of plant *Spilanthus calva*, *Spilanthus oleraceae*, *Urtica dioica*, *Piper longum* and *Gymnema sylvestre* are mixed in equal proportion along with conventional additives to form an topical and intradermal injection form. The composition can be used as topical or ointment or spray forms.

The formulation can be used as an analgesic when applied for muscular pains and inflammation. The formulation is used against toothache and gum trouble. The formulation has specific gravity ranging between 0.897-1.127 and refractive index ranging between 1.1325-1.3642.

The additives used in the cream/ointment selected from a group consisting of poly ethylene glycol bases, hydro emulsifying bases and bentonite. The additives used in the intradermal injection being sterile water for injection. The additives used are water-soluble bases, selected from the group consisting of tragacanth, pectin, acacia and gelatin.

The formulation at dose of 400 mg/kg did not show any toxicity in rats as well as no change in organ body weight. The formulation at a dose ranging from 100-200 mg/kg is highly effective as local anaesthetic for around 5-7 min.

Anaesthesia is induced by administering an effective amount of the formulation to patient together with or in combination with therapeutically acceptable additives.

The herbal formulation comprises *Spilanthus calva* (3%) and *Spilanthus oleraceae*, (3%) with conventional additives at a dose ranging from 100-200 mg/kg being moderately effective as local anaesthetic for around 20 min.

The formulation containing *Spilanthus calva* (3%), *Spilanthus oleraceae* (3%), *Gymnema sylvestre* (3%) with conventional additives at a dose ranging from 100-200 mg/kg is moderately effective as local anaesthetic for around 15 min.

The formulation can be used as an anaesthetic at a dose ranging from 100-200 mg/kg body weight is effective as local anaesthetic around for 5-20 min.

The invention is further illustrated by the following non-limiting examples.

| Formulation (F1) | |
|---|---|
| *Spilanthus calva* | 3 wt. % |
| Simple ointment base | 97.0% |

*Spilanthus calva* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Mix the plant extract and dissolve them in simple ointment base. Then solution and add specified quantity of water to make 100 ml. The formulation is useful to a Local anesthetic.

The formulation F1 is effective for only 15 minutes observed from the time that is 30 to 45 minutes only, the results can be seen in the table 1.

| Formulation (F2) | |
|---|---|
| *Spilanthus oleraceae* | 3 wt. % |
| Simple ointment base | 97.0% |

*Spilanthus oleraceae* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Mix the plant extract and dissolve them in simple ointment base. Then solution and add specified quantity of water, required amount of water to make 100 ml. The formulation is useful to a Local anesthetic. Accordingly, the investigation deals with the topical application/intradermal injection of the formulation.

The formulation F2 is effective for only 15 minutes observed from the time that is 30 to 45 minutes only, the results can be seen in the table 1.

| Formulation (F3) | |
|---|---|
| *Piper longum* | 1 wt. % |
| Simple ointment base | 99.0% |

*Piper longum* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Mix the plant extract and dissolve them in simple ointment base. Then solution and add specified quantity of water, required amount of water to make 100 ml. The formulation is useful to a Local anesthetic. Accordingly, the investigation deals with the topical application/intradermal injection of the formulation. Kindly refer to table 1 and 2.

The formulation F3 is effective for only 15 minutes observed from the time that is 30 to 45 minutes only, the results can be seen in the table 1.

| Formulation (F4) | |
|---|---|
| *Gymnema sylvestre* | 3 wt. % |
| Simple ointment base | 97.0% |

*Gymnema sylvestre* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Mix the plant extract and dissolve them in simple ointment base. Then solution and add specified quantity of water, required amount of water to make 100 ml. The formulation is useful to a Local anesthetic. Accordingly, the investigation deals with the topical application/intradermal injection of the formulation.

The formulation F4 is effective for only 30 minutes observed from the time that is 30 to 60 minutes only, the results can be seen in the table 1.

| Formulation (F5) | |
|---|---|
| *Urtica dioica* | 3 wt. % |
| Simple ointment base | 97.0% |

*Urtica dioica* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Mix the plant extract and dissolve them in simple ointment base. Then solution and add specified quantity of water, required amount of water to make 100 ml. The formulation is useful to a Local anesthetic. Accordingly, the investigation deals with the topical application/intradermal injection of the formulation.

The formulation F5 is effective for only 40 minutes observed from the time that is 20 to 60 minutes only, the results can be seen in the table 1.

| Formulation (F6) | |
|---|---|
| *Spilanthus calva* | 3 wt. % |
| *Spilanthus oleraceae* | 3 wt. % |
| Simple ointment base | 94.0% |

*Spilanthus calva* and *Spilanthus oleraceae* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Mix the plant extract and dissolve them in simple ointment base. Then solution and add specified quantity of water, required amount of water to make 100 ml. The formulation is useful to a Local anesthetic. Accordingly, the investigation deals with the topical application/intradermal injection of the formulation.

The formulation F6 is effective for only 40 minutes observed from the time that is 20 to 60 minutes only, the results can be seen in the table 1.

| Formulation (F7) | |
|---|---|
| *Spilanthus calva* | 3 wt. % |
| *Spilanthus oleraceae* | 3 wt. % |
| *Gymnema sylvestre* | 3 wt. % |
| Simple ointment base | 91.0% |

*Spilanthus calva*, *Spilanthus oleraceae* and *Gymnema sylvestre* were collected and dried in shade. The dried material (1 Kg) is then powdered and extracted with 50% aqueous alcohol (3 L) for 5 days. At the end of this, the solvent is decanted and filtered if necessary to remove the plant debris.

The extract is then concentrated under vacuum at less than 50° C. Then the extract is lyophilised to obtain the extract in powder form.

Mix the plant extract and dissolve them in simple ointment base. Then solution and add specified quantity of water, required amount of water to make 100 ml. The formulation is useful to a Local anesthetic. Accordingly, the investigation deals with the topical application/intradermal injection of the formulation.

The formulation F7 is effective for only 45 minutes observed from the time that is 15 to 60 minutes only, the results can be seen in the table 1.

| Formulation (F8) | |
| --- | --- |
| *Spilanthus calva* | 3 wt. % |
| *Spilanthus oleraceae* | 3 wt. % |
| *Gymnema sylvestre* | 3 wt. % |
| *Urtica dioica* | 3 wt. % |
| *Piper longum* | 1 wt. % |
| Simple ointment base | 87.0% |

*Spilanthus calva, Spilanthus oleraceae, Gymnema sylvestre, Urtica dioica* and *Piper longum* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Mix the plant extract and dissolve them in simple ointment base. Then solution and add specified quantity of water, required amount of water to make 100 ml. The formulation is useful to a Local anesthetic. Accordingly, the investigation deals with the topical application/intradermal injection of the formulation.

The formulation F8 is effective for 120 minutes observed from the time that is 5 to 120 minutes, and it is reversible at 120 minutes and therefore, it is highly effective than the other formulations evident from the table 1.

TABLE 1

Effect of formulation(s) on Local anesthetic properties using infiltration anesthesia on guinea pig wheal method (n = 6).

| Drug | Treatment group (100 mg/ kg · b · wt) | Time in minutes after topical application | | | | | | | |
| --- | --- | --- | --- | --- | --- | --- | --- | --- | --- |
| | | 0 | 5 | 10 | 15 | 20 | 30 | 45 | 60 | 120 |
| Control | | + | + | + | + | + | + | + | + | + |
| Formulation | F1 | + | + | + | + | + | − | − | + | + |
| | F2 | + | + | + | + | + | − | − | + | + |
| | F3 | + | + | + | + | + | − | − | + | + |
| | F4 | + | + | + | + | + | − | − | − | + |
| | F5 | + | + | + | + | − | − | − | − | + |
| | F6 | + | + | + | + | − | − | − | − | + |
| | F7 | + | + | + | − | − | − | − | − | + |
| | F8 | + | − | − | − | − | − | − | − | − |
| Lignocaine | 2% w/w | + | + | − | − | − | − | − | − | − |

Formulation (F1) contains *Spilanthus calva* (3%) balance being conventional additives. Formulation (F2) contains *Spilanthus oleraceae* (3%) balance being conventional additives. Formulation (F3) contains *Gymnema sylvestre* (3%) balance being conventional additives. Formulation (F4) contains *Piper longum* (1%) balance being conventional additives. Formulation (F5) contains *Urtica dioica.* (3%) balance being conventional additives. Formulation (F6) contains *Spilanthus calva* (3%) and *Spilanthus oleraceae*, (3%) balance being conventional additives. Formulation (F7) contains *Spilanthus calva* (3%), *Spilanthus oleraceae* (3%), *Gymnema sylvestre* (3%) balance being conventional additives. Formulation (F8) contains *Spilanthus calva* (3%), *Spilanthus oleraceae* (3%), *Urtica dioica* (3%), *Gymnema sylvestre* (3%) and *Piper longum* (3%) balance being conventional additives.

The results of the present study (table 1) demonstrated that in the control group the animals showed immediate response when plicking from 5, 10 to 60 min. therefore, a positive (+) response is recorded, showing no anesthetic activity. Where as, the formulation F1 shows the loss in sensation (−) from 30 min onward.

Therefore F1 formulation is effective at 30 min, and useful as a local anesthetic. The formulation F8 at a dose of 100 mg/kg is highly effective as it shows at 5 min, even F6 & F7 shows at 20 and 15 min respectively where as F1 to F5 showed effect at 30 min (Table 1).

Note: No mortality/gross abnormality were observed in the animals during the treatment of formulation (F8) containing formulation.

Local Anesthetic Activity:

Intra Dermal Wheal Method in Guinea Pigs:

The hairs on the back of guinea pigs were shaved. The normal response of the animal with a pinprick on both sides of the back was tested with 0.2 ml of the herbal formulations were injected intradermally on the left side and 0.2 ml of a normal saline (0.9%) was injected on the right side of the back. The sides were demarcated by ink. Six pinpricks were applied at interval of 2 to 3 s. Pinpricks were repeated after every 5 min. Animals showing no squeak response to all the six pinpricks were considered positive to anaesthetic effect. (Bandana M, et al., 2003)

TABLE 2

Effect of formulation (s) on Local anesthetic properties using infiltration anaesthesia on guinea pig wheal method (n = 6).

| Drug | Treatment group (mg/kg) | Time in minutes after intradermal injection | | | | | | | |
| --- | --- | --- | --- | --- | --- | --- | --- | --- | --- |
| | | 0 | 5 | 10 | 15 | 20 | 30 | 45 | 60 |
| Control | | + | + | + | + | + | + | + | + |
| F6 | 25 | + | + | + | + | + | + | − | − |
| | 50 | + | + | + | + | + | − | − | − |
| | 100 | + | + | − | − | − | − | − | − |
| F7 | 25 | + | + | + | + | + | − | − | − |
| | 50 | + | + | + | + | − | − | − | − |
| | 100 | + | − | − | − | − | − | − | − |
| F8 | 25 | + | + | + | + | − | − | − | − |
| | 50 | + | + | + | − | − | − | − | − |
| | 100 | + | − | − | − | − | − | − | − |
| Lignocaine | 2% w/w | + | − | − | − | − | − | − | − |

Since F6, F7 and F8 were found effective further dose dependent studies have been taken up.

The formulation (F6) contains *Spilanthus calva* (3%) and *Spilanthus oleraceae*, (3%) with balance being conventional additives The formulation (F7) contains *Spilanthus calva* (3%), *Spilanthus oleraceae* (3%), *Gymnema sylvestre* (3%) with balance being conventional additives.

The formulation (F8) contains *Spilanthus calva* (3%), *Spilanthus oleraceae* (3%), *Urtica dioica* (3%), *Gymnema sylvestre* (3%) and *Piper longum* (3%) with balance being conventional additives.

The formulation F8 is highly effective (Table 2) and it is safe.

Note: No mortality/gross abnormality was observed in the animals during the treatment of formulation (F8) containing formulation.

Disadvantages of Lignocaine: Dizziness, abnormal sensation like burning, pricking, pervertal sensation and in severe case will ultimately lead to epileptic seizures.

Advantages of F8 herbal formulation: Recovery time is very fast and it does not cause any burning or dizziness.

TABLE 3

Effect of formulations (F6, F7 and F8) on relative mean ± SEM organ weights of rats (n = 6)

| Treatment group (400 mg/kg) | Body weight (g) | Kidney (g) | Liver (g) | Spleen (g) |
|---|---|---|---|---|
| Control | 156.3 ± 9.2 | 0.83 ± 0.05 | 6.32 ± 0.64 | 0.72 ± 0.07 |
| F6 | 167.0 ± 8.6 | 0.85 ± 0.07 | 5.93 ± 0.87 | 0.64 ± 0.08 |
| F7 | 149.8 ± 7.6 | 0.87 ± 0.08 | 6.21 ± 0.72 | 0.83 ± 0.06 |
| F8 | 155.2 ± 9.5 | 0.89 ± 0.08 | 6.06 ± 0.89 | 0.75 ± 0.05 |

The formulation (F6) contains *Spilanthus calva* (3%) and *Spilanthus oleraceae*, (3%) with balance being conventional additives. Formulation (F7) contains *Spilanthus calva* (3%), *Spilanthus oleraceae* (3%), *Gymnema sylvestre* (3%) with balance being conventional additives. Formulation (F8) contains *Spilanthus calva* (3%), *Spilanthus oleraceae* (3%), *Urtica dioica* (3%), *Gymnema sylvestre* (3%) and *Piper longum* (3%) with balance being conventional additives.

The results of the table 3 shows there is no significant changes in body weight of various vital organs in the body in toxicity studies.

The formulation F6, F7 and F8 is highly effective (Table 3) and it is safe (Table 3).

Note: No mortality/gross abnormality was observed in the animals during the treatment of formulations (F6, F7 and F8).

We Claim:

1. An herbal local anesthetic formulation comprising extracts of *Spilanthes calva* (1-3 wt %), *Spilanthes oleraceae* (1-3wt %), *Urtica dioica* (2-3 wt %), *Piper longum* (1-2 wt %) and *Gymnema sylvestre* (2-3 wt %) in pharmaceutically acceptable dosage form, optionally further comprising an additive.

2. The herbal formulation as claimed in claim 1, wherein the extract of *Spilanthes calva* is obtained from leaves, roots, flowers, rhizome and/or fruits.

3. The herbal formulation as claimed in claim 1, wherein the extract of *Piper longum is obtained from the fruit thereof.*

4. The herbal formulation as claimed in claim 1, wherein the extract of *Spilanthes leraceae* is obtained from leaves, flowers, rhizome and/or unripe fruits.

5. The herbal formulation as claimed in claim 1, wherein the extract of *Gymnema sylvestre* is obtained from aerial parts thereof.

6. The herbal formulation as claimed in claim 1, wherein the extracts of *Spilanthes calva, Spilanthes oleraceae, Piper longum, Urtica dioica* and *Gymnema sylvestre* are mixed with the additive to provide a topical application or intradermal injection form.

7. The herbal formulation as claimed in claim 1, wherein the said formulation has a specific gravity ranging between 0.897-1.127.

8. The herbal formulation as claimed in claim 1, wherein the formulation has a refractive index ranging between 1.1325-1.3642.

9. The herbal formulation as claimed in claim 1, wherein the formulation is a cream or ointment and wherein the additive is selected from the group consisting of poly ethylene glycol bases, hydro emulsifiying bases and bentonite.

10. The herbal formulation as claimed in claim 6, wherein the additive is in the intradermal injection is sterile water.

11. The herbal formulation as claimed in claim 1, wherein additive is selected from the group consisting of tragacanth, pectin, acacia and gelatin.

12. The herbal formulation as claimed in claim 1 wherein said composition is used in the form of topical ointment or spray.

13. The herbal formulation as claimed in claim 1, wherein the formulation at a dose of 400 mg/kg does not show any toxicity in rats.

14. The herbal formulation as claimed in claim 1, wherein the formulation at a dose ranging from 100-200 mg/kg is effective as a local anaesthetic for around 5-7 minutes.

15. A method of effecting local anesthesia for 5-20 minutes comprises administering the herbal formulation as claimed in claim 1 at a dose ranging from 100-200 mg/kg body weight.

\* \* \* \* \*